United States Patent [19]

Lehtikoski et al.

[11] Patent Number: 5,026,455
[45] Date of Patent: Jun. 25, 1991

[54] METHOD FOR AUTOMATIC DETERMINATION OF THE DRY PULP CONTENT, THE INFILTRATION CAPACITY AND THE WIRE RETENTION OF A PULP SUSPENSION

[75] Inventors: Olavi Lehtikoski; Pekka Lehtikoski, both of Varkaus, Finland

[73] Assignee: Lehtikoski Development OY, Varkaus, Finland

[21] Appl. No.: 301,129

[22] Filed: Jan. 25, 1989

[30] Foreign Application Priority Data

Feb. 2, 1988 [FI] Finland .................................. 880480

[51] Int. Cl.$^5$ ........................... D21F 1/08; G01N 5/00
[52] U.S. Cl. ...................................... 162/49; 162/258; 162/263; 73/63; 73/61 R; 73/61.4
[58] Field of Search ................. 162/258, 263, 198, 49; 73/61 R, 63, 61.4

[56] References Cited

U.S. PATENT DOCUMENTS

| | | | |
|---|---|---|---|
| 3,488,078 | 12/1969 | Sepall et al. | 162/252 |
| 3,893,333 | 7/1978 | Sunahara et al. | 73/61 R |
| 4,114,427 | 9/1978 | Iguchi et al. | 162/263 |
| 4,409,853 | 10/1983 | Chase et al. | 162/263 |
| 4,662,991 | 5/1987 | Karna et al. | 162/49 |
| 4,704,899 | 11/1987 | Burr et al. | 73/61 R |
| 4,708,011 | 11/1987 | Rautakorpi et al. | 162/263 |

FOREIGN PATENT DOCUMENTS

| | | |
|---|---|---|
| 2830553 | 2/1979 | Fed. Rep. of Germany . |
| 67957 | 2/1985 | Finland . |
| 71019 | 7/1986 | Finland . |
| 72813 | 3/1987 | Finland . |
| 1397347 | 6/1975 | United Kingdom . |

*Primary Examiner*—Steve Alvo
*Attorney, Agent, or Firm*—Cushman, Darby & Cushman

[57] ABSTRACT

A method and an apparatus for the automatic determination of the dry pulp content, the infiltration capacity and the wire retention of a pulp suspension. In the method the automatically or manually taken pulp suspension sample is brought to the sample container (2) of the determination equipment (1) located in the immediate neighborhood of the production or the operation process. According to the invention the quantity of the sample in the sample container is measured by weighing, the sample is in case of need attenuated into the processing consistency range, a part of the sample is led to the filter (4), is filtrated in the filter with and/or without a filtering paper, the sample cake obtained is transferred to the desiccator (8) and dried with the desiccator, the dried sample cake is weighed and the test results are written out with the output equipment (11). To the equipment in accordance with the invention belongs a cabinet-like basic unit, inside the basic unit placed on a scale mounted sample containers (2), a filter station (3, 4, 5, 6), an evaporization station (8), a scale station (9), a filtering paper storage depot (7) and inside the basic unit movable made conveyor unit (12).

7 Claims, 1 Drawing Sheet

METHOD FOR AUTOMATIC DETERMINATION OF THE DRY PULP CONTENT, THE INFILTRATION CAPACITY AND THE WIRE RETENTION OF A PULP SUSPENSION

The object of the invention is to provide a method for determining of the dry content, the filtration capacity and the wire retention of a pulp suspension or corresponding substances and for making of a dried test cake in connection with the production or use of pulp, in which method an automatically or manually taken pulp suspension sample is brought into the sample container of the determination equipment, which is placed in the immediate neighbourhood of the production or operation process. Additionally the object of the invention is to provide equipment for application of the method.

Nowadays the quality control of paper-making pulp and the like is as follows: The pulp sample is brought from the production process and firstly the dry content is determined out of it manually by using the Büchner filter funnel. After that out of the remaining sample the infiltration capacity is determined either with the help of a CF-apparatus, a Schopper-Riegler instrument or with a sheet mould. When performing this with the help of the sheet mould a sample sheet for the other tests is obtained at the same time, otherwise it has if needed to be made separately. The wire retention is in quality control generally not determined, partly because of its laboriousness, partly because of the very reason, that the benefit of its continuous testing is not as big as that of the testing of the dry content and the infiltration capacity. The results are often confirmed by making double determinations. When the results have been calculated, they are often entered from a terminal into a computer system. The acquisition of the sample, the testing and the calculation of the results take in general from half an hour to one hour.

The greatest disadvantages of the present method are its slowness, the big amount of work it requires and the human errors occurring when applying it. From the point of view of the regulation of the quality of the pulp the present method is irretrievably slow, especially in the consistency regulation of the pulps this drawback has proved to be very bad. The need for a big amount of work binds the personnel and causes costs to arise, and the sampling frequency cannot anyway be kept high enough. To provide for human errors the regulation measures must be taken very carefully, which further adds to the delay in rectifications.

The purpose of the invention is to bring about a method, by which the afore mentioned, with the earlier methods connected disadvantages are removed. In particular the aim of the invention is to bring forth a method, with the help of which the dry content, the filtration capacity and the wire retention of the pulp suspension is determined quickly and in a dependable way as well as automatically. Further the purpose of the invention is to bring forward an equipment for the application of the method, which equipment is favourable to produce and to use as well as reliable in operation.

In the method in accordance with the invention the amount of the sample in the sample container is measured by weighing, the sample is, if required, attenuated into the processing consistency range, a part of the sample is conducted to the filter, is filtrated on the filter with and/or without the filtering paper, the sample cake obtained is transferred to the desiccator and is dried with the desiccator, the dried sample cake is weighed and the testing results are written out with the output equipment. With the method in accordance with the invention the following advantages are achieved:

1. The method speeds considerably up the determination of the dry content and the filtration capacity of the pulp suspension and gives at the same time to the results a greater reliability than earlier. In this way for the part of the consistency and the filtration capacity of the pulps a quality regulation in the cathegory of the double compared with the earlier is made possible.

2. Because when applying the method all the operations connected with the method—the sampling, the processing of the sample, the performance of the determinations, the calculation and recording of the results as well as the rectification measures to be taken—can be automated, thus compared with the traditional way labour and costs are saved.

In a favourable application of the invention the time of filtration is measured several times during the filtration process, until the whole sample lot has been filtrated. In addition to the one value, the development of the filtration capacity is obtained to describe the filtration capacity as a function of the pulp quantity filtrated on the wire.

In an other favourable application of the invention by means of a conveyor unit on the filter a filtering paper is transferred and the fine substance, which in the filtration performed without the filtering paper along with the filtrate has gone through the wire to the filtrate container, is conducted to the filter. With the help of a process of this kind the fine substance is determined and the wire retention can be calculated.

In the following the method in accordance with the invention is explained more in detail by referring to the drawing.

DETAILED DESCRIPTION

Figure 1:
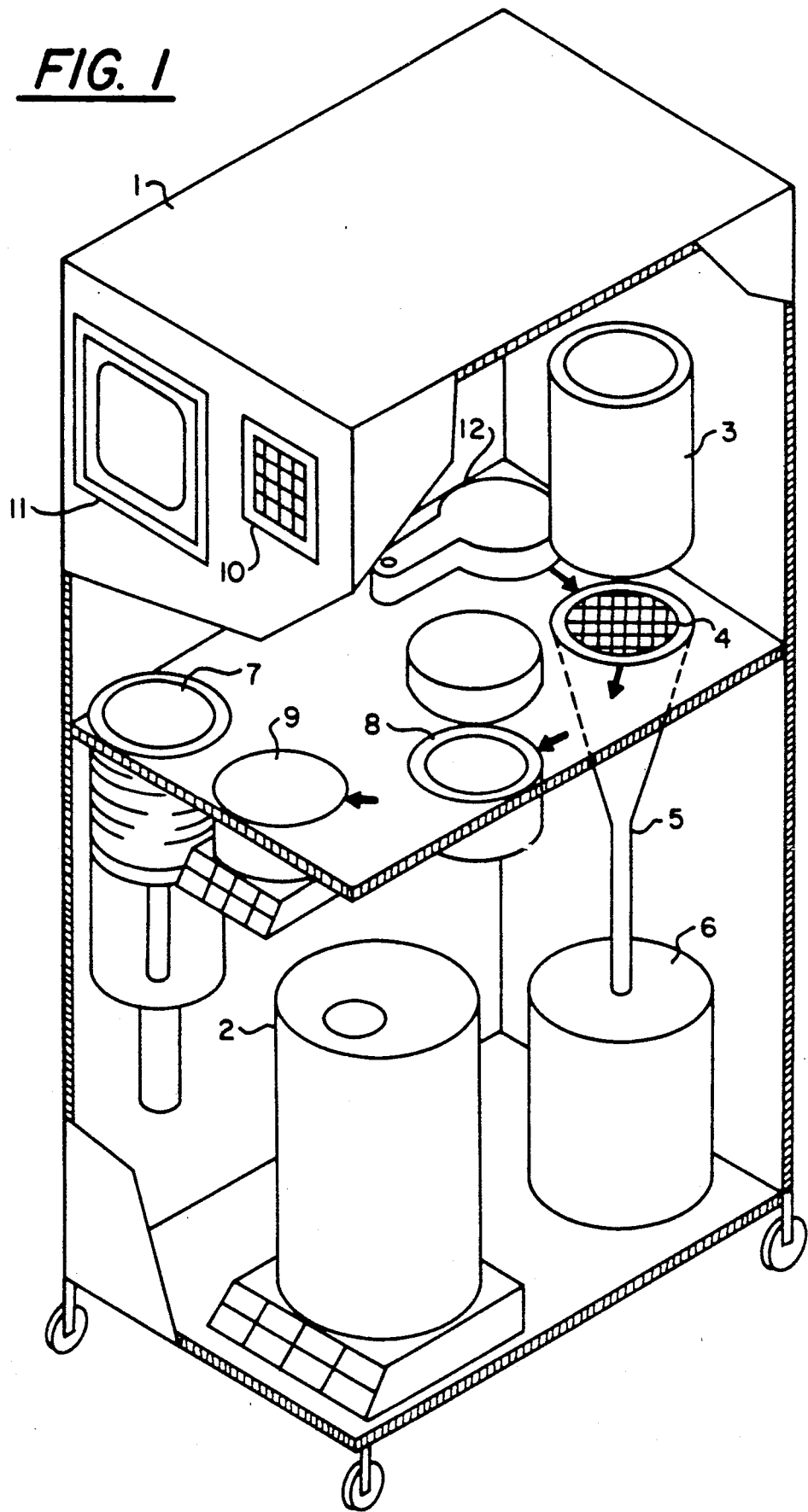
FIG. 1 presents one embodiment of the apparatus for the application of the method, in accordance with the invention.

To the equipment presented in the figure belongs a movable cabinet 1, which on its one side has a door equipped with a window. The actual determination equipment is placed inside the cabinet. The sample container 2 has been mounted on a scale. In some applications there are sample containers more than one. The filter station consists of an upper cylinder 3, a with a wire equipped filter part 4, a suction stem 5 and a filtrate container 6. The filtering paper storage depot 7 consists of a storage cylinder for the filtering paper pile and an automatic elevation mechanism for the pile. To the evaporization station 8 belong a heating plate, low pressure connections and a water- or a Peltier-condenser. To the scale station 9 belongs a scale. These stations are in connection with a computer, the keyboard 10 and display 11 of which are to be seen on the figure. The conveyor unit 12 is arranged to be movable around its centre axle guided by the computer to the afore mentioned stations placed on the orbit of a circle: the filter station, the evaporization station, the scale station, the filtering paper station. In addition to the above mentioned parts to the equipment belong further the compressed air and the low pressure equipments, the electronics and the electric inputs. The compressed air can also be taken from an external network.

The operation of the equipment in accordance with the method takes place for instance in the following way: The pulp suspension sample is poured by hand or led along a pipe from the automatic sampling element to the container 2. With the help of the scale of the container knowledge of the quantity of the sample is obtained. The sample characteristic is fed in with the computer from the keyboard 10. In connection with the automatic sampling the input of the characteristic separately is not required.

The processing and determinations of the sample take place in the equipment in the form of a sequential proceeding. The pulp suspension in the container 2 is attenuated in case of need to a consistency level suitable for the determinations by leading into the container a wished quantity of water or possibly of the filtrate from the container 6. The suction stem 5 is filled with water or with filtrate led from the container 6. The selected quantity of the diluted sample is conducted from the container 2 by pumping with a pump or with the help of the compressed air to the upper cylinder 3 of the filter station. If so wished, the sample can still be attenuated in the upper cylinder. The sample is mixed favourably for instance with air. The valve located in the suction stem 5 is opened, whereby the filtration starts. During the filtration the height of the fluid surface level is read as a function of the time and in this way the filtration speed is obtained as a function of the pulp quantity of the cake. After the filtration the conveyor unit 12 is brought to the filter station and with the wire sheet of the unit the filter cake is pressed at the same time connecting on the low pressure of the filter part 4. After the elapse of a suitable time low pressure is connected to the conveyor unit and in the filter part pressure instead of low pressure. In this way the filter cake is transferred to be transported by the conveyor unit and by moving the conveyor unit it is brought to the evaporization station 8. There the fibre cake formed on the wire is dried and after drying weighed on the weighing station 9.

Simultaneously with the drying of the fibre cake a second parallel sequence of determination is commenced. The conveyor unit is moved to the filtering paper storage depot 7, from where a filtering paper is taken on it and the filtering paper is transferred to the filter station. Following the filtrate from the container 6 is led to the upper cylinder 3. The filtration of it with the filtering paper, the drying and the weighing is performed as has been presented before. In this way the fine substance quantity passed through the wire can be measured and the wire retention be calculated.

As a third phase, if so wished, as a parallel to the drying of the second phase the filtration, the drying and the weighing with the use of the filtering paper is commenced. In this manner the total substance quantity is obtained, with which as a balance checking the added together amount obtained in the first and the second phase of the material quantities remained on the wire and passed through the wire is compared.

In the method the filtration time is measured several times during the proceeding of the filtration process. The filtration time can be measured for instance when half of the sample has been filtrated, when ¾ of the sample has been filtrated, when ⅞ of the sample has been infiltrated and when the whole sample has been filtrated. Hereat in addition to the one value to describe the filtration capacity the development of the filtration capacity as a function of the pulp quantity filtrated on the wire is obtained.

The determinations from the same sample are repeated, if so wished, several times. When the sample pulp suspension is not needed anymore the rest is emptied for instance in the sewer and the equipment is cleaned automatically. After this the equipment can be used for the processing of the following sample.

At the analyzing of the sample all the three filtrations are not necessarily needed to be performed, if not the balance checking is wished. For instance for the determination of the consistency one filtration is sufficient.

The method in accordance with the invention can be also applied to the processing of other samples than the pulp samples, as for example for different kinds of precipitations, suspensions and colloids. Out of these especially the determination of solid substances in the waste water is worth while mentioning.

The invention has been described above by referring to one favourable application. The invention is, however, not limited to the presented application, but it can vary within the inventional concept defined by the patent claims.

I claim:

1. A method for determining the dry pulp content, the filtration capacity and the wire retention of a pulp suspension and for making a dried test cake in connection with the production or use of pulp comprising:

providing a pulp suspension sample;

placing the pulp suspension sample in a sample container;

measuring the quantity of the sample in the sample container by weighing;

diluting the sample to a predetermined processing consistency range, the diluted sample having a height of a fluid surface level in the sample container;

filtrating a portion of the sample to provide a sample cake;

transferring the sample cake obtained to a desiccator;

drying the sample cake with the desiccator;

weighing the dried sample cake to determine a dry pulp content of the cake; and generating an output from the foregoing test results, wherein during the step of filtrating, the height of the fluid surface level is read as a function of time so that filtration speed as a function of dry pulp content of the cake can be determined.

2. A method as in claim 11, wherein said step of filtrating comprises filtrating with a wire screen on a filter part, said method further including the step of measuring filtration time several times during the filtration process; and determining the filtration capacity as a function of pulp quantity filtrated on the wire.

3. A method as in claim 1, wherein said step of filtrating comprises filtrating with a filter paper brought into a filter from a storage station by a conveying unit.

4. A method as in claim 3, wherein said step of filtrating comprises filtrating with a wire screen on a filter part, the fine substance passed through the wire screen along with the filtrate to a filtrate container being lead to the filter paper where at the fine substance is determined and the wire retention can be calculated.

5. A method as in claim 1, wherein the dry pulp content of the pulp suspension sample is determined by using a filtering paper and is also determined without using a filter paper, and the fine substance is determined from the filtrate, whereby a balance checking can be performed on the results.

6. A method in accordance with claim 1, wherein following said step of filtrating, liquid collected during said filtrating step is fed to a filtering paper so as to collect fine substances passed with fluid during the filtration process so that material retained in the fluid during the filtration process can be calculated.

7. A method in accordance with claim 6, wherein the dry pulp content of the pulp suspension sample is determined by determining the weight of the pulp cake in combination with the weight of the material filtered by said filtering paper.

* * * * *